(12) United States Patent
Sedelmayer

(10) Patent No.: US 6,241,519 B1
(45) Date of Patent: Jun. 5, 2001

(54) METHOD OF DETERMINING THE APPROXIMAL PASSABILITY OF AN INTERDENTAL SPACE

(75) Inventor: Jiri Sedelmayer, Hamburg (DE)

(73) Assignee: Curaden AG, Kriens (CH)

( * ) Notice: Subject to any disclaimer, the term of this patent is extended or adjusted under 35 U.S.C. 154(b) by 0 days.

(21) Appl. No.: 09/155,990

(22) PCT Filed: Apr. 8, 1997

(86) PCT No.: PCT/CH97/00137

§ 371 Date: Feb. 1, 1999

§ 102(e) Date: Feb. 1, 1999

(87) PCT Pub. No.: WO97/37612

PCT Pub. Date: Oct. 16, 1997

(30) Foreign Application Priority Data

Apr. 10, 1996 (CH) ...................................... 906/96

(51) Int. Cl.⁷ .................................................. A61C 19/04
(52) U.S. Cl. .............................................. 433/72; 433/141

(58) Field of Search ............................. 433/72, 141, 147, 433/148, 149, 286

(56) References Cited

U.S. PATENT DOCUMENTS

| 4,805,252 |   | 2/1989 | Tarrson et al. .          |
|-----------|---|--------|--------------------------|
| 5,035,616 | * | 7/1991 | Woelfel ................... 433/72 |
| 5,044,951 | * | 9/1991 | Sheridan ................... 433/72 |
| 5,752,832 | * | 5/1998 | Vardimon et al. ................ 433/72 |

* cited by examiner

Primary Examiner—Nicholas D. Lucchesi

(57) ABSTRACT

Flexible probing elements (4.1, ..., 4.6) with different diameters are guided into an interdental space for determining a proximal allowance of the interdental space. The proximal allowance is determined according to the parameter values that correspond to the probing element that just barely fits through the interdental space. The probing elements (4.1, ..., 4.6) can be realized on a probing tip (3) with a diameter that changes continuously or in a stepwise manner. The determination of the proximal allowance makes possible for an adviser to determine in an exact and reproducible manner the optimum interdental brush for the user.

20 Claims, 2 Drawing Sheets

METHOD OF DETERMINING THE APPROXIMAL PASSABILITY OF AN INTERDENTAL SPACE

This application is the national phase under 35 U.S.C. §371 of prior PCT International Application No. PCT/CH97/00137 which has an International filing date of Apr. 8, 1997 which designated the United States of America, the entire Contents of which are hereby incorporated by reference.

The solution according to the invention is defined by means of the features of claim 1.

The core idea of the invention consists in that the proximal allowance of the concerned interdental spaces is measured. For this purpose, different probing elements with pregiven parameters are guided into the interdental space. The proximal allowance is determined by that element (or its parameter) that can just barely be guided into the interdental space.

Preferably, all the interdental spaces are measured and entered into a schematic that is provided to the user. The corresponding type of interdental brush can be entered instead of the measuring value or the proximal allowance. In this way, the user obtains from the adviser the information about which interdental brush will provide an optimum cleaning of which interdental spaces.

Particularly suited for carrying out the process is a device wherein the probing elements are realized in the shape of sections of different diameter. The diameter can be modified by steps or continuously along the length of the probe. Advantageously, the probe elements have a flexibility corresponding to the one of the interdental brushes. The probing elements consist purposefully of a plastic (for example, polyamide), but can also be manufactured of metal.

However, the probing elements can also be realized as a set of probes with several individual probing elements of different diameters. Purposefully, several probing devices are provided with several probing elements.

The probes can be firmly or exchangeably attached to the handle. In the first case, a probing tip can be arranged at each end of the elongated handle. The probing tips are shaped in such a way that they are completely covered (or at least partially) with separate diameter regions. In the second case, the probe has a head that is structured for inserting into an interdental brush holder.

Other advantageous embodiments and features result from the following detailed description and the totality of the claims.

BRIEF DESCRIPTION OF THE DRAWINGS

The drawings are used for further explaining the embodiments, wherein.

The same parts are basically referred to with the same reference numerals in the figures.

WAYS FOR CARRYING OUT THE INVENTION

Figure 1:
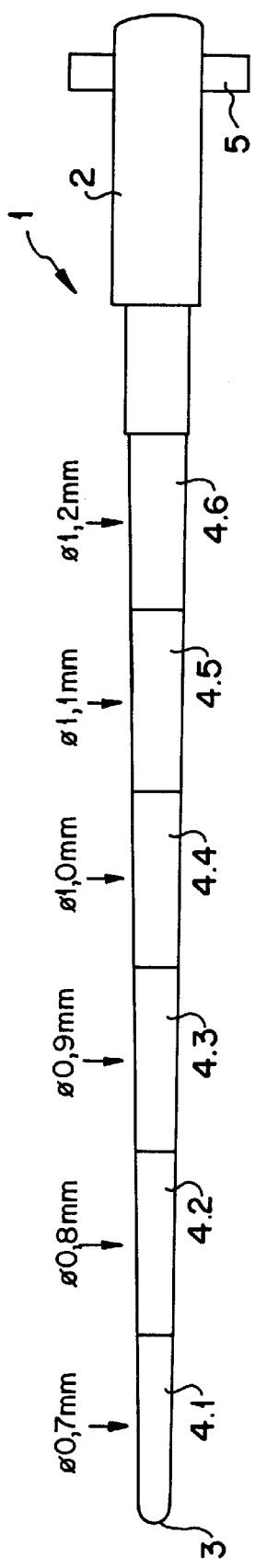
FIG. 1 is a schematic representation of a probing device with a diameter that varies continuously along the length of the probe.

FIG. 1 shows a probing device 1 with a head 2, which can be exchangeably attached to a holder (not shown). The attachment element 5 on the head 2 can be shaped as a kind of traverse, collar, or another traversal element, which makes possible the anchoring of the head in the holder, for example, according to WO 86/0232 or U.S. Pat. No. 4,805, 252.

The probing device 1 has a long thin probing tip 3 with a diameter that varies along the longitudinal direction. In this example, the diameter increases continuously from the rear (that is, from the head 2) toward the front. Six probing elements 4.1 to 4.6, for example, with a length of, for example, 3 mm are formed. The diameter in the center of the probing element 4.1 to 4.6 increases, for example, from the rear to the front by 1/10 mm each time. The probing element 4.1 closest to the front has, for example, a center diameter of 0.7 mm and the rearmost probing element 4.6 has a diameter of, for example, 1.2 mm.

The probing elements 4.1 to 4.6 are preferably color coded. The probing tip 3 is also divided in the longitudinal direction into sections with different colors.

The length of the section should at least be as great as the "passage length" of the interdental space in the probing direction. That is, a probing element should reach—as far as its diameter is smaller than the allowance of the interdental space—completely through the interdental space.

It must be taken into consideration that the interdental spaces can be confusing (for example, if a concave proximal side of a first tooth connects to a convex proximal surface of a second tooth). In such a case it must be confirmed without doubt which probing element can be just barely completely introduced through the interdental space. From what was said it can be inferred that the probing elements 4.1 to 4.6 must be flexible. However, the deformability of the cross section must be minimal. The probing tip 3 should preferably be manufactured from a plastic with corresponding properties (that is, polyamide).

Figure 2:
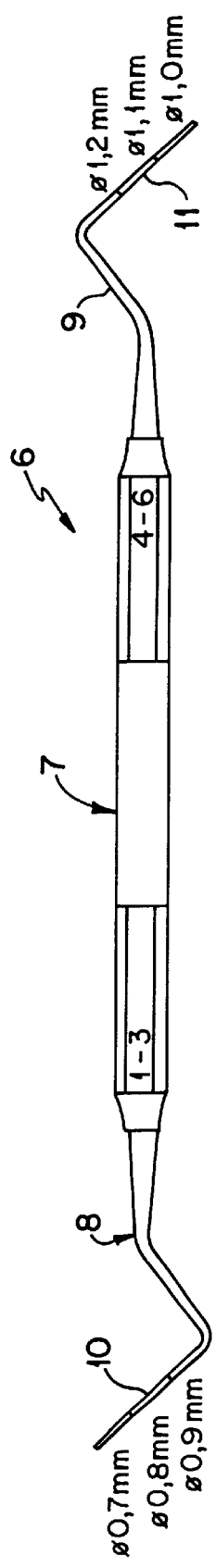
FIG. 2 is a schematic representation of an instrument with two probing devices.

FIG. 2 shows an instrument 6 with a handle 7 and two probing devices 8, 9. These are attached at both ends of the handle 7. According to a preferred embodiment, they are shaped at an angle so that they can reach well into the interdental spaces of the molars. Each of the probing devices 8, 9 ends in a probing tip 10, 11.

Figure 3:
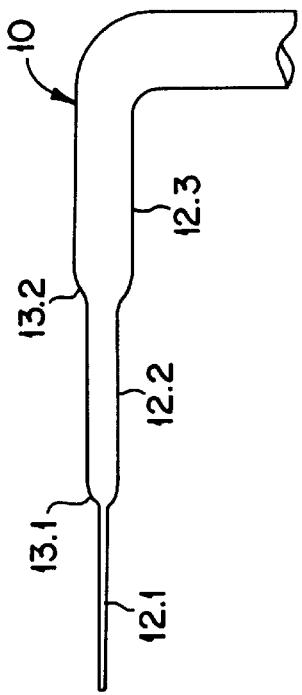
FIG. 3 is a schematic representation of a probing device of the instrument according to FIG. 2.

FIG. 3 shows in very enlarged representation an exemplary probing tip 10. It is provided, for example, with three probing elements 12.1, 12.2, 12.3, each with a different diameter. Each probing element 12.1, 12.2, 12.3, however, has a constant diameter over its total length. That is, the probing element 12.1, for example, has a constant diameter of 0.7 mm, the probing element 12.2 a diameter of 0.8 mm, and the third probing element 12.3 has a diameter of 0.9 mm. Stepwise transitions 13.1, 13.2 are formed in between. These transitions have a rounded shape. For the purpose of an easier visual recognition, the probing elements 12.1, 12.2, 12.3 can have different colors. They can be coded by means of different color rings. The color rings are preferably also provided on the corresponding interdental brushes, which will be used by the user after the proximal allowance has been determined.

Both probing tips 10 and 11 of the instrument 6 are shaped differently. In this way, for example, the probing tip 10 can cover a first diameter series (0.7 mm, 0.8 mm, 0.9 mm) and the second probing tip 11 can cover a second diameter series (1.0 mm, 1.1 mm, 1.2 mm).

It can also be conceived that each probing tip can have a constant diameter along its total length (so that only one probing element can be realized). A set of several probing tips is required then for analyzing an interdental space or all the teeth.

The use of the device according to the invention is, in principle, very easy. The adviser (pharmacist, dentist, dental hygienist) measures the proximal allowance of the interdental space by guiding the probing tip into the interdental space and determines which probing element fits just barely through the interdental space. He/she may have to guide several probing tips through the interdental space until the allowance is determined. With instrument 6 according to FIG. 2, for example, only one turn is needed to switch back and forth between two probes. If a probing tip only has one probing element, then the instrument may have to be put down several times during the examination.

Figure 4:
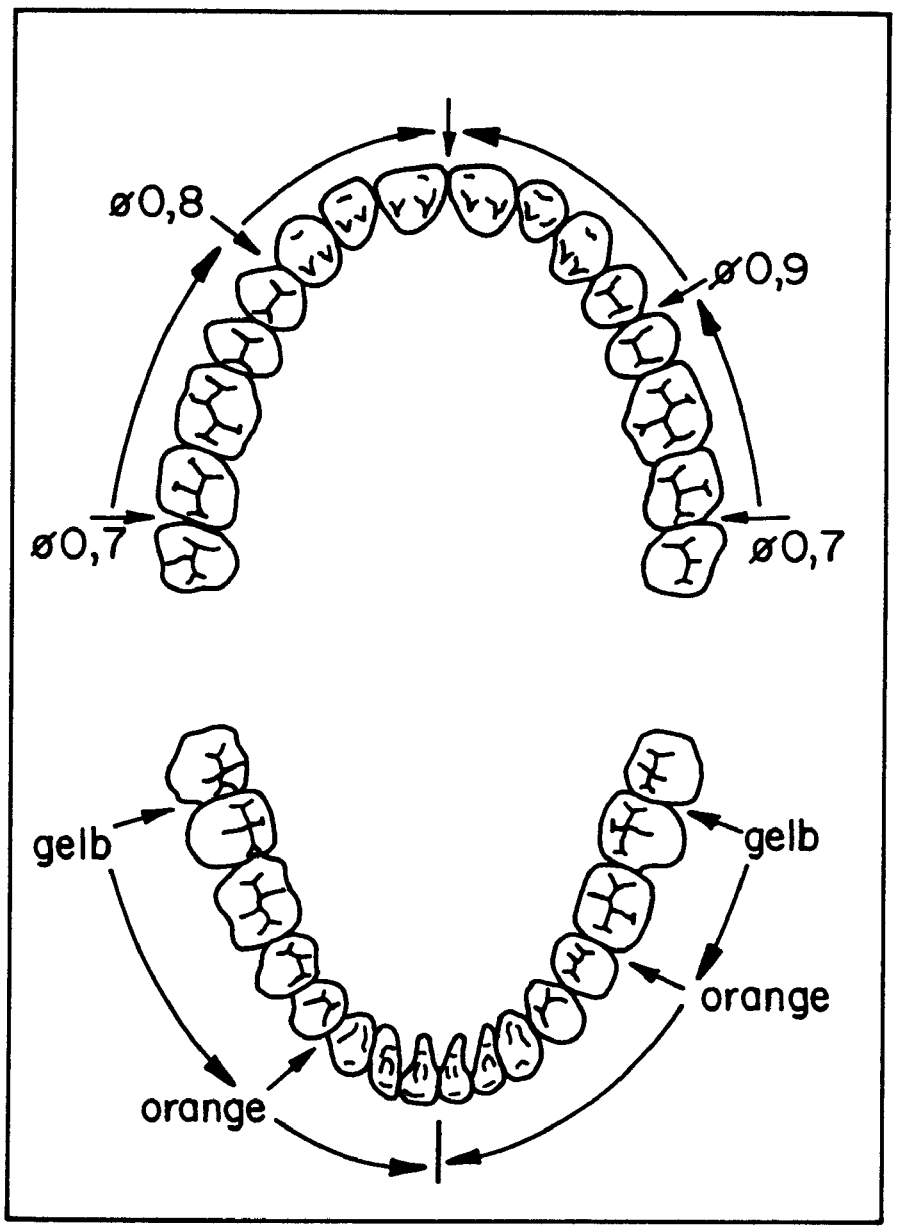
FIG. 4 is a schematic representation of the measured proximal allowance.

To retain the determined values in a manner that is easy to read for the user, they can be drawn beside the corresponding interdental spaces in a known dental schematic (compare with FIG. 4, for example). If a color coding is provided, the corresponding colors (compare "yellow", "orange" in FIG. 4) can be noted in the schematic (which is preferably also done by the manufacturer to designate the corresponding brush type).

The user purchases the corresponding interdental brush and is sure that he/she has made an optimum choice.

Since it is the declared object of the invention to determine the optimum interdental cleaning device, it is advantageous if—as mentioned—the manufacturer designates the interdental brushes, for example, with the code that corresponds to the proximal allowance.

To summarize, it should be remembered that a simple method for determining a proximal allowance is provided by means of the invention, which makes possible for the user to utilize the optimum dental cleaning device. The instruments for carrying out the process are also technically simple and easily operated.

What is claimed is:

1. A dental hygiene system comprising:
   at least one interdental probe for measuring an interdental space, said interdental probe including a flexible probe tip divided into a plurality of segments, each segment having a respective characteristic diameter, the system further comprising a plurality of said interdental brushes, each said interdental brush being associated with a respective said segment of said flexible probe tip; and
   at least one interdental brush associated with said characteristic diameter of said interdental probe.

2. The system according to claim 1, wherein said flexible probe tip is made from a substantially incompressible material.

3. The system according to claim 1, wherein said plurality of segments decrease in diameter in a direction towards a distal end of said probe tip.

4. The system according to claim 3, wherein said plurality of segments decrease stepwise in diameter.

5. The system according to claim 3, wherein said plurality of segments decrease continuously in diameter.

6. The system according to claim 1, comprising a handle member, said flexible probe tip being mounted on an end of said handle member.

7. The system according to claim 6, comprising two said flexible probe tips mounted on opposite ends of said handle member.

8. The system according to claim 6, wherein said flexible probe tip is replaceably mounted on said handle member.

9. The system according to claim 1, wherein said flexible probe tip is made from a flexible plastic.

10. The system according to claim 9, wherein said flexible probe tip is made from a polyamide.

11. The system according to claim 1, wherein said plurality of segments are color-coded with respect to their respective diameters.

12. The system according to claim 1, wherein said probe comprises a flexible probe tip having a single characteristic diameter.

13. The system according to claim 12, wherein said flexible probe tip is made from a substantially incompressible material.

14. The system according to claim 12, comprising a handle member, said flexible probe tip being mounted on an end of said handle member.

15. The system according to claimed 14, wherein said flexible probe tip is replaceably mounted on said handle member.

16. The system according to claim 14, comprising two said flexible probe tips mounted on opposite ends of said handle member.

17. The system according to claims 16, wherein one said flexible probe tip has a different characteristic diameter from the other said probe tip.

18. The system according to claim 12, wherein said flexible probe tip is made from a flexible plastic.

19. The system according to claim 12, wherein said flexible probe tip is color-coded in accordance with said single characteristic diameter thereof.

20. The system according to claim 1, wherein each said segment is color-coded so as to correspond with a respective said interdental brush.

* * * * *